United States Patent [19]

Murphy et al.

[11] Patent Number: 4,552,757

[45] Date of Patent: Nov. 12, 1985

[54] USE IN AN ANIMAL HOST AND PRECURSORS FOR VACCINES UTILIZING AVIAN-HUMAN REASSORTANTS TO COMBAT INFLUENZA A VIRUS

[75] Inventors: Brian R. Murphy; Robert M. Chanock, both of Bethesda, Md.; Robert G. Webster, Memphis; Virginia S. Hinshaw, Germantown, both of Tenn.

[73] Assignee: St. Jude Children's Research Hospital, Memphis, Tenn.

[21] Appl. No.: 563,370

[22] Filed: Dec. 20, 1983

[51] Int. Cl.[4] ............................................ A61K 39/145
[52] U.S. Cl. ....................................................... 424/89
[58] Field of Search ............................................ 424/89

[56] References Cited

U.S. PATENT DOCUMENTS 3,992,522 11/1976 Chanock et al. ...................... 424/89
4,318,903 3/1982 Lobmann et al. ..................... 424/89
4,338,296 9/1982 Lobmann et al. ..................... 424/89
4,341,870 7/1982 Wyatt et al. ......................... 435/237

OTHER PUBLICATIONS

Murphy et al., *Infection and Immunity*, 37:1119–1126, Sep. 1982.
Murphy et al., *Science*, 218:1330–1332, Dec. 24, 1982.
Hinshaw et al., C.A. 99, #118900r, (1983), Virology, 1983, 128(1):260-3, Altered Tissue Tropism of Human–Avian Reassortant Influenza Viruses.
Kim et al., C.A. 87, #148423q, (1977) Izv. Akad. Naukkaz. Ssr. Ser. Biol., 1977, 15(4):29–35, Effect of Physicochemical Factors on the Enzymic Activity of Influenza Virus from Man and Birds and Their Recombinants.
Podchernyaeva, C.A. 92 #211654d, (1980).

*Primary Examiner*—Shep K. Rose
*Attorney, Agent, or Firm*—John S. Roberts, Jr.

[57] ABSTRACT

A method of producing a vaccine useful in animals which comprises producing a reassortment by gene exchange from an avian influenza A virus parent and an animal influenza A virus parent and then selecting for the reassortant containing two animal surface antigen genes and six avian internal genes by temperature and antibodies.

6 Claims, No Drawings

USE IN AN ANIMAL HOST AND PRECURSORS FOR VACCINES UTILIZING AVIAN-HUMAN REASSORTANTS TO COMBAT INFLUENZA A VIRUS

This application is related to a companion application Ser. No. 563,372 filed Dec. 20, 1983 and entitled "Human Use of Avian-Human Reassortants as Vaccines for Influenza A Virus."

The present invention relates specially to avian-human influenza reassortant viruses which may be used in the nature of vaccines. In this application the human virus is considered generally, i.e., as example of a non-avian, or animal, influenza virus. The viruses produced are live, attenuated, immunogenic but poorly transmissible. In general, a living cell is coinfected with an avian virus and a human wild-type virus, and the resulting reassortant is selected by a temperature control which, in several cases, shuts off replication of the human parent at 42° C. whereas replication of the human parent occurs at 37° C. Additionally, antibodies specific to the surface antigens of the avian parent have been utilized. It has been found that these reassortants show use for vaccines commercially. Additional research studies were made utilizing squirrel monkeys (lower primates) in which attenuation of the reassortants was demonstrated and resistance to wild-type virus challenge was induced.

STATEMENT OF DEPOSIT

Prior to filing this application and on Oct. 6, 1983, the inventors made a deposit at the American Type Culture Collection, Rockville, Md. This deposit is made under the patent protocol of the ATCC restricting distribution of samples until the issue of a patent when unrestricted use thereof is then directed. Deposit of A/Washington/897/80 X A/Mallard/New York/6750/78 (H3N2) reassortant received ATCC No. VR2072; and deposit of A/California/10/78 X A/Mallard/New York/6750/78 (H1N1) reassortant received ATCC No. VR2073.

MATERIAL INFORMATION DISCLOSURE

U.S. Pat. No. 4,318,903 Löbmann et al discloses CNCM I-062 strain of influenza virus vaccine prepared by recombination of A/PR/8/34 X A/Alaska/5/77. These two virus strains are human strains differing from the present avian-human reassortant.

U.S. Pat. No. 4,338,296 Löbmann et al discloses CNCM N° I-099 prepared by recombination of influenze A/PR/8/34 X A/California/10/78 and again the recombinant is human/human.

U.S. Pat. No. 3,992,522 Chanock et al.

U.S. Pat. No. 4,341,870 Wyatt et al.

Murphy et al, *Infection and Immunity*, 37:1119–1126, September 1982, is a preliminary study *prior to the utilization of reassortants* wherein avian influenza A virus in squirrel monkeys and hamsters were compared with human influenza A virus.

Murphy et al, *Science*, 218:1330–1332, Dec. 24, 1982, is a preliminary work showing related work on avian-human reassortants.

DISCLOSURE OF THE INVENTION

The present invention denotes renewed interest in the development of a live attenuated influenza A virus vaccine since current inactivated influenza virus vaccines do not provide complete protection and do not appear to retain their effectiveness when administered annually. Although genes bearing temperature-sensitive mutations have been transferred to a series of new epidemic wild-type viruses and have rendered such viruses satisfactorily attenuated for man, the genetic instability of the attenuated phenotype represents an insoluble problem. Live attenuated influenza A viruses have been produced by transfer of genes from an attenuated donor virus to new epidemic influenza A viruses. Since resistance to influenza A virus is mediated by the development of an immune response to the hemagglutinin (HA) and neuraminidase (NA) glycoproteins, live, attenuated reassortant vaccine strains were selected in which genes for these surface antigens were derived from the epidemic virus, while the non-surface protein ("internal") genes were derived from the attenuated parent. This process of gene exchange is readily achieved with influenza A viruses since they possess a segmented genome consisting of eight negative-stranded RNA segments that code for at least ten proteins.

There is a need for stable attenuated viruses that are unable to escape their attenuation phenotype. Many of the influenza A virus genes that have evolved over a long period in birds differ significantly in nucleotide sequence from corresponding genes of human and animal influenza A viruses. Because of these marked differences, some avian influenza viruses are expected to replicate inefficiently in animal cells and thereby be attenuated. Such attenuated avian viruses are also expected to retain their attenuated characteristics after limited replication in man.

This concept was evaluated in animals, including squirrel monkeys, ducks, ferrets, and swine, among others. It was initially evaluated in squirrel monkeys because this primate develops illness similar to humans after experimental infection with influenza A viruses. Ten avian influenza A viruses were evaluated in squirrel monkeys, and a spectrum of replication was observed (Table 1). Some avian influenza viruses replicated almost as well as the human influenza A virus. However, several avian influenza A viruses grow at least 1,000 times less efficiently than human influenza A viruses. Studies were commenced with these latter avian influenza A viruses with the intent of producing avian-human reassortant viruses that are attenuated for man and that could be used as live virus vacccine strains. Restriction of replication of the avian-human reassortant vaccine virus in the primate respiratory tract would be effected by naturally occurring avian influenza virus genes rather than by mutant genes selected by limited passage of virus in an unnatural host.

In preventing influenza A virus by the reassortant technique, it is noted that here both temperature and antibodies were utilized to select for desired reassortant viruses, the former to eliminate the human virus parent and the latter to eliminate the avian parent. In the present case working with influenza A virus, the initial replication temperature for the reassortant product was 37° C. Upon raising the temperature to 42° C., the human virus present in the progeny after coinfection by both human and avian parents fails to replicate and the utilization of antibodies against the avian parent inhibits its replication. In this way, only reassortant viruses are selected.

TABLE 1
EFFICIENCY OF PLAQUE FORMATION OF AVIAN AND HUMAN INFLUENZA A VIRUSES IN TISSUE CULTURE AND THEIR LEVEL OF REPLICATION IN SQUIRREL MONKEYS

| Influenza A Virus* | Antigenic Subtype | Reduction of Plaque Formation+ at 42° C. Compared to 37° C. ($Log_{10}$) | Mean $Log_{10}$ Titer of Virus ($TCID_{50}$/ml) in Tracheal Lavage Fluid |
|---|---|---|---|
| Avian | | | |
| MAL/573/78 | H1N1 | 0.2 | 1.5 |
| MAL/6750/78 | H2N2 | 0.0 | 2.4 |
| PIN/286/78 | H4N8 | 0.0 | 2.4 |
| PIN/358/79 | H3N6 | 0.0 | 2.8 |
| MAL/827/78 | H8N4 | 0.6 | 2.9 |
| PIN/119/79 | H4N6 | −0.1 | 3.0 |
| TUR/5/79 | H10N7 | −0.1 | 3.1 |
| MAL/88/76 | H3N8 | 0.2 | 4.3 |
| MAL/6874/78 | H3N2 | 0.0 | 4.4 |
| PIN/121/79 | H7N8 | 0.0 | 5.0 |
| Human | | | |
| Udorn/307/72 | H3N2 | >4.6 | 6.5 |
| Wash/897/80 | H3N2 | >5.8 | 5.7 |

+On MDCK or primary chicken kidney cell culture
*Each virus tested in at least four squirrel monkeys One avian influenze A virus, A/Mallard/New York/6750/78 (H2N2), that was markedly restricted in replication in the trachea of squirrel monkeys, was evaluated as a donor of its non-surface protein genes for attenuation of virulent human influenza A viruses for the squirrel monkey. Avian-human reassortant influenza viruses were produced by mating the avian influenza virus and a virulent human influenza virus in primary chick kidney culture at 37° C. and selecting progeny at 42° C. in the presence of antibodies to the surface antigens of the avian parent virus. The utilization of antibodies as an assistant in the selection process is deemed of easy recognition except in their role as assistants to the temperature selection. As seen in Table 1, 42° C. is restrictive for replication of human influenza A viruses. In matings involving three different virulent human influenza viruses (Table 2), each reassortant virus isolated derived its surface antigen genes from its human influenza virus parent and its "internal" genes from its avian parent virus. Such reassortants will be referred to as "six-gene" reassortants. Like their avian influenza parent virus, each of the avian-human reassortant influenza viruses produced plaques efficiently at 42° C. indicating that one or more of the avian influenza genes that code for non-surface proteins specify growth at 42° C. The level of replication of two avian-human reassortant influenza viruses in the lower respiratory tract of the squirrel monkey was compared to that of their parental viruses (Table 3). The two avian-human reassortant influenza viruses were as restricted in growth in the monkey's trachea as their avian influenza parent viruses. In each instance the reassortant viruses were shed in lower titer and for a shorter duration than the human influenza virus parent. These findings indicate that restriction of replication of the avian influenza virus is a function of one or more of its "internal" genes. To investigate which of the avian genes was responsible for restricted replication in primates, reassortant viruses were produced that contained human influenza virus surface antigens from the A/Udorn/72 (H3N2) virus and one or more of the internal genes derived from the avian influenza virus parent (Table 4). Avian-human reassortant viruses that contained only an RNA 1, RNA 3, or non-structural (NS) protein RNA 8 segment of avian influenza origin did not exhibit restriction (i.e., they grew to the same level as their human influenza A/Udorn/72 parent). In contrast, avian-human reassortants that contained only the avian nucleoprotein (NP) or matrix (M) protein RNA segment were as restricted in their growth as their avian influenza parent. Avian-human reassortant influenza viruses containing two or more genes derived from their avian influenza parent virus were restricted in replication if they possessed an NP or M gene from the avian parent (Table 5). In addition, the reassortant possessing the RNA 1 and NS genes from the avian parent manifested significant restriction of virus replication in the trachea. This suggests that specific genes, that by themselves do not restrict replication, can act together to effect a reduction in replication. Table 6 shows infection with avian-human influenza reassortant virus induces resistance to challenge with wild type human influenza virus parent.

Avian-human reassortant viruses were produced by mating the A/Mallard/Alberta/573/78 (H1N1) or A/Pintail/Alberta/121/79 (H7N8) avian virus with the A/Udorn/307/72 (H3N2) human virus. Reassortant viruses containing the hemagglutinin and neuraminidase genes from the human virus and the other six RNA segments from the avian parent were evaluated for their level of replication in the upper and lower respiratory tract of squirrel monkeys (Table 7). Each reassortant virus replicated to a level in the lower respiratory tract comparable to its avian parent (Table 8). For these two avian viruses and another examined (A/Mallard/New York/6750/78) (see Table 2), the non-surface antigen genes of the avian parental virus are the primary determinants of the level of replication in squirrel monkeys suggesting that this might be a general phenomenon applicable to many other avian influenza viruses. These results have implications for the use of avian influenza A viruses as donors of genes to attenuate epidemic human viruses.

The term precursor, as used in this specification and claims, denotes a composition less developed than a vaccine (for human use) and is a composition designed for prevention of disease in animals. The companion case mentioned above describes how these precursors (vaccines for animals) were developed into the vaccines (for humans).

TABLE 2

CONSISTENT TRANSFER OF 6 "INTERNAL" AVIANΔ INFLUENZA VIRUS GENES TO AVIAN-HUMAN INFLUENZA VIRUS REASSORTANTS WITH H1N1 OR H3N2 SURFACE ANTIGENS

Genotype of Avian-Influenza Reassortants from Mating of Avian Influenza Virus with Indicated Wild Type Human Influenza Virusɸ

| Gene | A/Udorn/72(H3N2) | A/Washington/80(H3N2) | A/California/78(H1N1) |
|---|---|---|---|
| PB2 | □ | □ | □ |
| PB1 | □ | □ | □ |
| PA | □ | □ | □ |
| HA | ■ | ■ | ■ |
| NA | ■ | ■ | ■ |
| NP | □ | □ | □ |
| M | □ | □ | □ |
| NS | □ | □ | □ |

Δ Avian virus was A/Mallard/New York/6750/78(H2N2)
■ = Gene derived from human wild type virus
□ = Gene derived from avian virus
ɸProgeny from indicated mating selected in the presence of antisera to avian influenza virus surface antigens at 42° C., a temperature restrictive for human influenza virus.

TABLE 3

RESTRICTION OF AVIAN-HUMAN INFLUENZA REASSORTANT VIRUSES IN SQUIRREL MONKEYS

| | | Virus Replication in Trachea | |
|---|---|---|---|
| Influenza A Virus | Number of Monkeys | Average Duration of Virus Shedding (Days) | Mean Peak Titer ($Log_{10}$ $TCID_{50}$/ml) of Tracheal Lavage Fluid |
| Avian A/Mallard/6750/78 | 7 | 2.6ɸ | 2.7ɸ |
| Reassortant | | | |
| A/Udorn/72 | 6 | 2.0ɸ | 2.2ɸ |
| A/Washington/80 | 8 | 2.3ɸ | 2.7ɸ |
| Human Wild Type | | | |
| A/Udorn/72 | 15 | 5.2 | 5.9 |
| A/Washington/80 | 14 | 5.6 | 5.7 |

NOTE:
Monkeys received $10^{7.0}$ $TCID_{50}$ of virus (0.5 ml intratracheally) and were infected in each instance.
ɸAvian virus and reassortants significantly restricted in growth compared to wild type human influenza viruses
Each reassortant contains 6 "internal" avian influenza virus genes.

TABLE 4

EFFECT OF SUBSTITUTION OF A SINGLE AVIAN INFLUENZA VIRUS GENE ON GROWTH OF HUMAN INFLUENZA A VIRUS IN MONKEYS

| | Parental Origin of Genes in Avian-Human Influenza Reassortant Viruses | | | | | | | | Virus Replication in Trachea | |
|---|---|---|---|---|---|---|---|---|---|---|
| Influenza VirusΔ | RNA1 | RNA2 | RNA3 | HA | NA | NP | M | NS | Average Duration of Virus Shedding (Days) | Mean Peak Titer ($Log_{10}$ $TCID_{50}$/ml) of Tracheal Lavage Fluid |
| Human | □ | □ | □ | □ | □ | □ | □ | □ | 5.3 | 5.1 |
| Avian-Human Reassortant | | | | | | | | | | |
| (a) 6 "internal" avian virus genes | ■ | ■ | ■ | □ | □ | ■ | ■ | ■ | 0.3* | 0.7* |
| (b) Single substitution of an avian virus gene | ■ | □ | □ | □ | □ | □ | □ | □ | 6.0 | 5.2 |
| | □ | ■ | □ | □ | □ | □ | □ | □ | 5.0 | 5.4 |
| | □ | □ | ■ | □ | □ | □ | □ | □ | 5.0 | 5.4 |
| | □ | □ | □ | □ | □ | ■ | □ | □ | 0.0* | 0.5* |
| | □ | □ | □ | □ | □ | □ | ■ | □ | 3.3*, 2.0*ɸ | 2.6*, 1.6*ɸ |
| | □ | □ | □ | □ | □ | □ | □ | ■ | 5.0 | 4.4 |

Avian Virus was A/Mallard/New York/6750/78(H2N2). Human Virus was A/Udorn/307/72(H3N2)
ΔEach virus tested in at least four squirrel monkeys
*Statistically significant difference from wild type human influenza virus
ɸ Two independently derived reassortants with this gene constellation
□ = Gene derived from human virus
■ = Gene derived from avian virus

TABLE 5

EFFECT OF VARIOUS CONSTELLATIONS OF AVIAN INFLUENZA VIRUS GENES ON GROWTH OF AVIAN-HUMAN INFLUENZA REASSORTANT VIRUSES IN MONKEYS

| Influenza VirusΔ | Parental Origin of Genes in Avian-Human Influenza Reassortant Viruses | | | | | | | | Virus Replication in Trachea | |
|---|---|---|---|---|---|---|---|---|---|---|
| | RNA1 | RNA2 | RNA3 | HA | NA | NP | M | NS | Average Duration of Virus Shedding (Days) | Mean Peak Titer (Log$_{10}$ TCID$_{50}$/ml) of Tracheal Lavage Fluid |
| Human | □ | □ | □ | □ | □ | □ | □ | □ | 5.3 | 5.1 |
| Avian-Human Reassortant | | | | | | | | | | |
| (a) 6 "internal" avian virus genes | ■ | ■ | ■ | □ | □ | ■ | ■ | ■ | 0.3* | 0.7* |
| (b) 2 or 3 "internal" avian virus genes | ■ | □ | □ | □ | □ | □ | □ | ■ | 3.5 | 3.2* |
| | □ | □ | ■ | □ | □ | □ | □ | ■ | 6.0 | 5.1 |
| | □ | □ | ■ | □ | □ | ■ | □ | ■ | 1.0* | 0.9* |
| (c) 5 "internal" avian virus genes | ■ | □ | □ | □ | □ | ■ | ■ | ■ | 2.0* | 1.7* |
| | ■ | □ | ■ | □ | □ | ■ | ■ | ■ | 0.5* | 0.8* |
| | □ | ■ | ■ | □ | □ | ■ | ■ | ■ | 2.0* | 1.7* |

Avian Virus was A/Mallard/New York/6750/78(H2N2). Human Virus was A/Udorn/307/72(H3N2).
ΔEach virus tested in at least four squirrel monkeys
*Statistically significant difference from wild type human influenza virus
□ = Gene derived from human virus
■ = Gene derived from avian virus

TABLE 6

INFECTION WITH AVIAN-HUMAN INFLUENZA REASSORTANT VIRUS INDUCES RESISTANCE TO CHALLENGE WITH WILD TYPE HUMAN INFLUENZA VIRUS PARENT

| Monkeys Administered 10$^7$ TCID$_{50}$ of Indicated Influenza Virus Intratracheally Four Weeks Pre-Challenge | Number of Monkeys | Virus Replication in Trachea after Intratracheal Administration 10$^{7.0}$ TCID$_{50}$ of Wild Type Human Influenza Virus | |
|---|---|---|---|
| | | Average Duration of Virus Shedding (Days) | Mean Peak Titer (Log$_{10}$ TCID$_{50}$/ml) of Tracheal Lavage Fluid |
| Human Wild Type VirusΔ | 6 | 0 | ≦0.5 |
| Avian-Human Reassortant | 5 | 0.4 | 1.0 |
| Avian Virus# | 2 | 6.0 | 3.8 |
| Placebo | 6 | 5.3 | 5.8 |

ΔHuman virus was A/Washington/897/80(H3N2)
Avian virus was A/Mallard/New York/6750/78(H2N2)

TABLE 7

GENOTYPE OF AVIAN-HUMAN INFLUENZA REASSORTANT VIRUSES

| | Genotype of Reassortant Virus Produced by Mating the Indicated Pair of Virusesφ | |
|---|---|---|
| Gene | A/Mallard/Alberta/573/78 × A/Udorn/307/72 | A/Pintail/Alberta/121/79 × A/Udorn/307/72 |
| PB2 | □ | □ |
| PB1 | □ | □ |
| PA | □ | □ |
| HA | ■ | ■ |
| NA | ■ | ■ |
| NP | □ | □ |
| M | □ | □ |
| NS | □ | □ |

□ = Gene derived from avian influenza virus; i.e., from the Mallard or Pintail virus
■ = Gene derived from human (A/Udorn/72) influenza virus
φProgeny from indicated mating selected in the presence of antisera to avian influenza virus surface antigens at 42° C., a temperature restrictive for human influenza virus.

TABLE 8

DECREASED REPLICATION OF AVIAN-HUMAN INFLUENZA REASSORTANT VIRUSES IN SQUIRREL MONKEYS

| Influenza Virus | Virus Replication in Trachea* | |
|---|---|---|
| | Average Duration of Virus Shedding (Days) | Mean Peak Titer (Log$_{10}$ TCID$_{50}$/ml) of Tracheal Lavage Fluid |
| Avian A/Mallard/78 | 2.7φ | 2.3φ |
| A/Mallard/78 × A/Udorn/72 Reassortant | 3.3φ | 3.4φ |
| Avian A/Pintail/78 | 4.7φ | 5.1φ |
| A/Pintail/78 × A/Udorn/72 Reassortant | 4.0φ | 4.8φ |

TABLE 8-continued

DECREASED REPLICATION OF AVIAN-HUMAN INFLUENZA
REASSORTANT VIRUSES IN SQUIRREL MONKEYS

| Influenza Virus | Virus Replication in Trachea* | |
|---|---|---|
| | Average Duration of Virus Shedding (Days) | Mean Peak Titer ($Log_{10}$ $TCID_{50}$/ml) of Tracheal Lavage Fluid |
| Human A/Udorn/72 | 6.0 | 6.3 |

NOTE:
Avian viruses were A/Mallard/Alberta/573/78(H1N1) and A/Pintail/Alberta/121/79(H7N8)
*Each virus tested in six squirrel monkeys
φSignificantly reduced compared to human influenza A/Udorn/72(H3N2) virus

We claim:

1. A vaccine for use in animals other than avians derived from an avian-human influenza reassortant virus whose non-surface protein genes are derived from the avian influenza virus A parent and the surface antigen genes are derived from the human influenza virus parent and where at least one of the avian influenza nucleoprotein and matrix protein genes are present in the reassortant, said avian-human influenza reassortant virus selected from one member of the group consisting of A/Washington/80 (H3N2) X A/Mallard/New York/6750/78 (H2N2); A/California/78 (H1N1) X A/Mallard/New York/6750/78 (H2N2); A/Udorn/307/72 X A/Mallard/Alberta/573/78; A/Udorn/307/72 X A/Pintail/Alberta/121/79; and A/Udorn/307/72 X A/Mallard/New York/6750/78 (H2N2).

2. A vaccine according to claim 1 wherein the avian-human influenza reassortant virus is A/Washington/80 (H3N2) X A/Mallard/New York/6750/78 (H2N2).

3. A vaccine according to claim 1 wherein the avian human influenza reassortant virus is A/California/78 (H1N1) X A/Mallard/New York/6750/78 (H2N2).

4. A vaccine according to claim 1 wherein the avian human influenza reassortant virus is A/Udorn/307/72 X A/Mallard/Alberta/573/78.

5. A vaccine acccording to claim 1 wherein the avian human influenza reassortant virus is A/Udorn/307/72 X A/Pintail/Alberta/121/79.

6. A vaccine according to claim 1 wherein the avian human influenza reassortant virus is A/Udorn/307/72 X A/Mallard/New York/6750/78 (H2N2).

* * * * *

UNITED STATES PATENT OFFICE
CERTIFICATE OF CORRECTION

Patent No. 4,552,757          Dated November 12, 1985

Inventor(s) BRIAN R. MURPHY, ROBERT M. CHANACK, ROBERT G. WEBSTER VIRGINIA S. HINSHAW It is certified that error appears in the above-identified patent and that said Letters Patent are hereby corrected as shown below:

IN THE ABSTRACT:

Line 2, "reassortment" should be --reassortant--.

Signed and Sealed this

Twenty-second Day of July 1986

[SEAL]

Attest:

Attesting Officer

DONALD J. QUIGG

Commissioner of Patents and Trademarks